United States Patent
Castillo et al.

(10) Patent No.: US 9,981,991 B2
(45) Date of Patent: May 29, 2018

(54) SYNTHESIS AND ISOLATION OF CRYSTALLINE ALKALI METAL ARENE RADICAL ANIONS

(71) Applicants: Efrain Maximiliano Castillo, El Paso, TX (US); Skye Fortier, El Paso, TX (US)

(72) Inventors: Efrain Maximiliano Castillo, El Paso, TX (US); Skye Fortier, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days. days.

(21) Appl. No.: 15/183,293

(22) Filed: Jun. 15, 2016

(65) Prior Publication Data
US 2016/0362428 A1 Dec. 15, 2016

Related U.S. Application Data

(60) Provisional application No. 62/175,888, filed on Jun. 15, 2015.

(51) Int. Cl.
*C07F 1/00* (2006.01)
*C07F 1/02* (2006.01)
*C07F 1/04* (2006.01)

(52) U.S. Cl.
CPC .................. *C07F 1/04* (2013.01); *C07F 1/00* (2013.01); *C07F 1/02* (2013.01); *C07B 2200/13* (2013.01)

(58) Field of Classification Search
None
See application file for complete search history.

(56) References Cited

PUBLICATIONS

Yokoi et al, Journal of the American Chemical Society (1998),120(48), pp. 12453-12458.*
Sather et al., "Dosage delivery of sensitive reagents enables glovebox-free synthesis," Nature, vol. 524, 2015, pp. 208-211.
Balk et al., "Electronic spectra of mono- and di-negative aromatic ions," Rcl. Tray. Chim. vol. 76, No. 10, 1957, pp. 813-823.
Loh et al., "Strong intramolecular calcium-π interactions with aryl substituents—requirements and limitations." Organometallics, vol. 33, 2014, pp. 14440-14449.
Hitchcock et al., "The first crystalline alkali metal salt of a benzenoid radical anion without a stabilizing substituent and of a related dimer: X-ray structures of the toluene radical anion and of the benzene radical anion dimer potassium-crown ether salts." J. Am. Chem. Soc., vol. 123, No. 1, 2001, pp. 189-190.
Rainis et al., "Disproportionation of the lithium, sodium, and potassium salts of anthracenide and perylenide radical anions in DME and THF," J. Am. Chem. Soc., vol. 96, No. 9, 1974, pp. 3008-3010.
Krieck et al., "Rubidium-mediated birch-type reduction of 1,2-diphenylbenzene in tetrahydrofuran." J. Am. Chem. Soc., vol. 133, No. 18, 2011, pp. 6960-6963.
Zabula, "A main group metal sandwich: five lithium cations jammed between two corannulene tetraanion decks." Science, vol. 333, No. 6045, 2011, pp. 1008-1011.
Connelly et al., "Chemical Redox Agents for Organometallic Chemistry." Chem. Rev., vol. 96, No. 2, 1996, pp. 877-910.
Kowalczuk et al., "New reactions of potassium naphthalenide with β-, γ- and δ-lactones: an efficient route to α-alkyl γ- and δ-lactones and α,β-unsaturated carboxylic acid esters," J. Org. Chem., vol. 57, No. 1, 1992, pp. 389-391.
Melero et al., "Structural characterization and bonding properties of lithium naphthalene radical anion, [Li$^+$(TMEDA)$_2$][C$_{10}$H$_8$(*)], and lithium naphthalene dianion [(Li$^+$TMEDA)$_2$C$_{10}$H$_8^{-2}$]." Dalton Trans. 2009, pp. 1286-1289.
Bock et al., "Single crystals of an ionic anthracene aggregate with a triplet ground state" Nature, vol. 404, No. 6775, 2000, pp. 267-169.
Scott et al., "After 118 years, the isolation of two common radical anion reductants as simple, stable solids." Chem. Commun. 2009, pp. 65-67.
Rosokha et al., "The question of aromaticity in open-shell cations and anions as ion-radical offsprings of polycyclic aromatic and antiaromatic hydrocarbons." J. Org. Chem. vol. 71, No. 25, 2006, pp. 9357-9365.
Soncini et al., "Ring-current aromaticity in open-shell systems," Chem. Phys. Lett. vol. 450, 2008, pp. 431-436.
Holy, "Reactions of the radical anions and dianions of aromatic hydrocarbons," Chem. Rev. vol. 74, No. 2, 1974, pp. 243-277.
Scott et al., "Sodium Naphthalene. I. A New Method for the Preparation of Addition Compounds of Alkali Metals and Polycyclic Aromatic Hydrocarbons," J. Am. Chem. Soc. vol. 58, No. 12, 1936, pp. 2442-2444.
Schlenk et al., "Über Metalladditionen an mehrfache Bindungen," Ber. Dtsch. Chem. Ges. vol. 47, No. 1, 1914, pp. 473.

* cited by examiner

*Primary Examiner* — Zinna Northington Davis
(74) *Attorney, Agent, or Firm* — Norton Rose Fulbright US LLP

(57) ABSTRACT

Certain embodiments are directed to a composition comprising a complex of the general formula [M(crown ether)(solvent)$_n$][arene$^-$], wherein M is an alkali metal and method of making the same.

4 Claims, 2 Drawing Sheets

A

B

C

D

SYNTHESIS AND ISOLATION OF CRYSTALLINE ALKALI METAL ARENE RADICAL ANIONS

This Application claims priority to U.S. Provisional Patent Application No. 62/175,888 filed Jun. 15, 2015, which is incorporated herein by reference in its entirety.

BACKGROUND

The reduction of aromatic hydrocarbons by alkali metals is known to generate reactive, organic radicals. These organic radicals are widely used reagents employed in a number of chemical reactions including, but not limited to, polymerization initiation, reductive metalation, ketyl-alkene cyclizations, lactone deprotonation, and reductive bond cleavage. These reagents are also important for modeling graphitic battery materials and are electrically conductive in solution. However, a notable drawback of these compounds is that they are very sensitive, rarely isolated, and must be prepared immediately prior to use. Their sensitivity and solution behavior complicates their use as chemical reagents and impedes their commercial sale.

Thus, additional stable alkali metal arene radical anion compositions and method of making such are needed.

SUMMARY

Arene radical monoanions, generated from the treatment of an aromatic hydrocarbon with an alkali metal, have been extensively studied over the past century for their unique electronic features. Moreover, these compounds are important chemical reagents that are routinely employed as potent one electron reductants. Despite their wide use and utility, these compounds are seldom isolated in the solid-state owing to their high reactivity and tendency to disproportionate.

The inventors have found that treatment of $M[arene^{-\bullet}]$ (M=alkali metal) with a crown ether readily provides $[M(crown\ ether)(solvent)_n][arene^{-\bullet}]$ as thermally stable, "bottleable" crystalline solids that can be stored indefinitely under inert conditions. In certain aspects the alkali metal is Li, Na, or K. In a further aspect the arene is biphenyl, naphthalene, anthracene, perylene. In still a further aspect the crown ether is 18-crown-6, 15-crown-5, or 12-crown-4 polyether. Demonstration of these methods and compositions provided by characterization of twelve radical arene complexes, described herein. The term "arene" is used herein generally to refer to an aromatic ring or multiple aromatic rings that are fused together. Examples of arenes include, for example, benzene, naphthalene, anthracene, biphenyl, perylene, and the like. The term arene also includes heteroarenes (i.e., aromatic compounds in which one or more of the carbon atoms in an aromatic ring has been replaced by a heteroatom, such as O, N, or S). Examples of heteroarenes include, for example, pyridine, furan, indole, benzimidazole, thiophene, benzthiazole, and the like. Crown ethers include 18-Crown-6, which is an organic compound with the formula $[C_2H_4O]_6$ and the IUPAC name of 1,4,7,10,13,16-hexaoxacyclooctadecane and polyclic amino ethers such as [2.2.2]Cryptand with the IUPAC name of 1,10-diaza-4,7,13,16,21,24-hexaoxabicyclo[8.8.8]hexacosane. Like other crown ethers, 18-crown-6 functions as a ligand for some metal cations with a particular affinity for potassium cations (binding constant in methanol: $10^6\ M^{-1}$). The term "solvent" refers to a polar, coordinating organic solvent and can include, but is not limited to tetrahydrofuran (THF), dimethyl ether ($OMe_2$), Diethyl Ether (Et2O), Dimethylformamide (DMF), N-Methylpyrrolidone (NME), Dimethoxyethane (DME), Hexamethylphosphoramide (HMPA), Dioxane, Diglyme, Triglyme, Tetraglyme, or Acetonitrile (MeCN).

The generality of the method has been demonstrated by the synthesis and isolation of 12 compounds utilizing a range of alkali metals and aromatic hydrocarbons. An additional benefit is the observation that when stored as solid, these compounds exhibit a markedly extended shelf life.

Certain embodiments are directed to a composition comprising a complex of the general formula $[M(crown\ ether)(solvent)_n][arene^{-\bullet}]$, wherein M is an alkali metal. In certain aspects the alkali metal is sodium (Na), lithium (Li), or potassium (K). In other aspect the solvent is a polar, coordinating organic solvent, in certain aspect the solvent is THF or DME. In other aspects the crown ether is 18-crown-6 polyether or any other crown ether that chelates an alkali metal. In certain aspect n is 1, 2, 3, 4, 5, or 6.

Other embodiments are directed to method of synthesizing crystalline alkali metal arene radical anions comprising: (a) reacting an alkali metal (M) with an arene forming an alkali metal-arene anion in an aprotic solvent; (b) adding a crown ether to the alkali metal-arene anion solution; (c) drying the crown ether/alkali metal-arene anion solution under vacuum forming a solid-state $[M(crown\ ether)(solvent)_n][arene^{-\bullet}]$, wherein M is an alkali metal. In certain aspects the crown ether is 18-crown-6 polyether or other crown ether capable of chelating an alkali metal. In certain aspects the alkali metal is lithium, sodium, or potassium. In a further aspect the arene is benzene, naphthalene, anthracene, biphenyl, or perylene.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
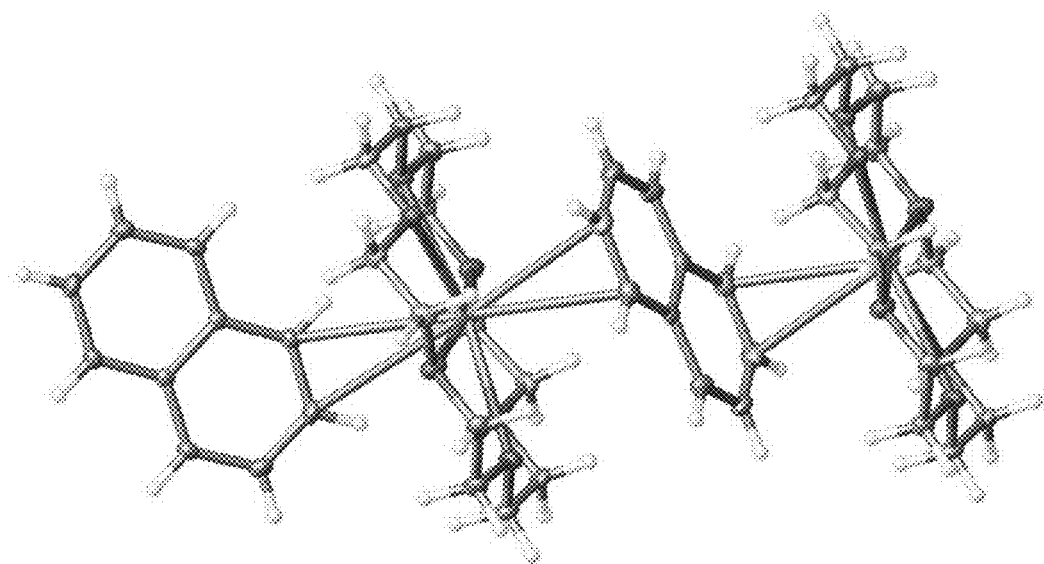
FIG. 1. Representative solid-state structures of (a) 3, (b) 4, (c) 8, and (d) 12.
Figure 1:
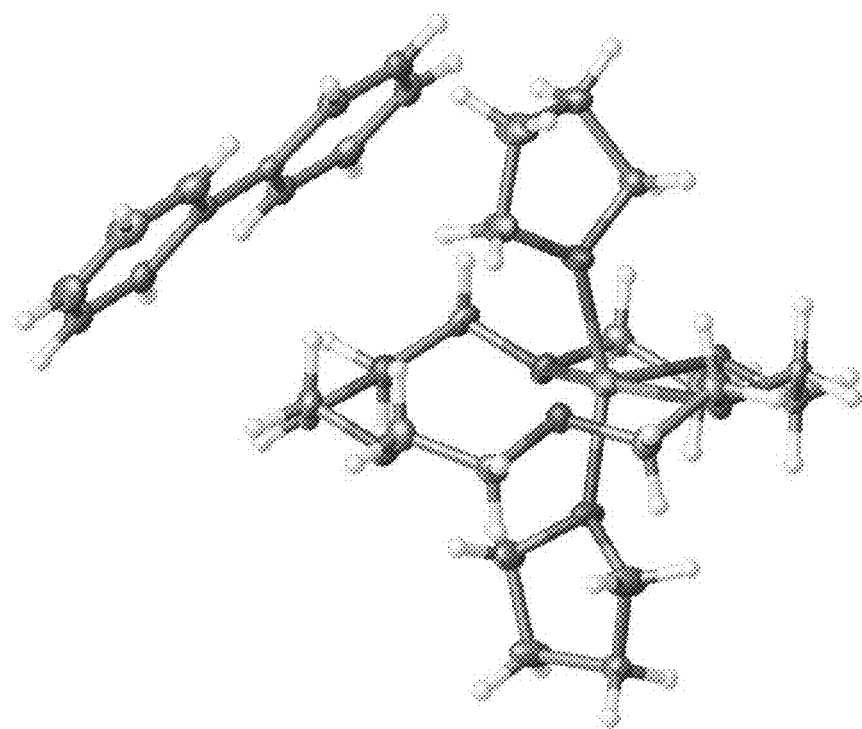
Figure 1:
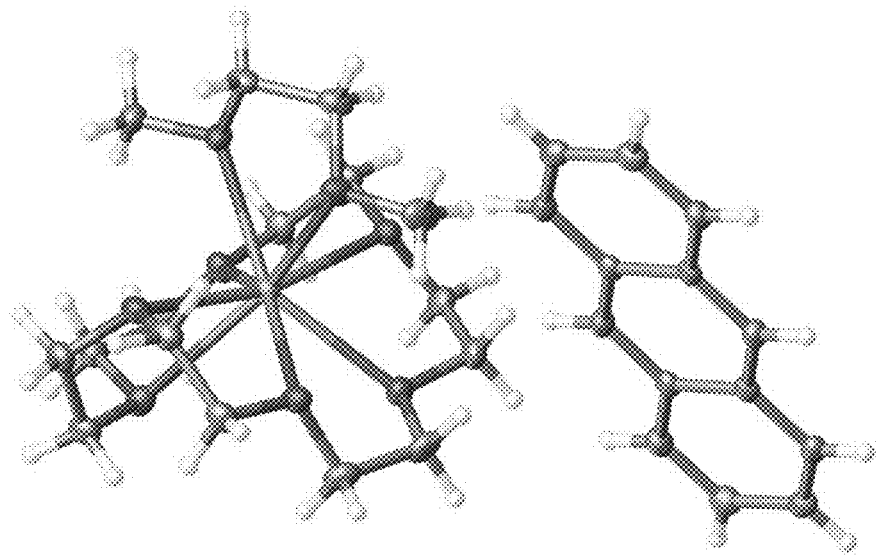
Figure 1:
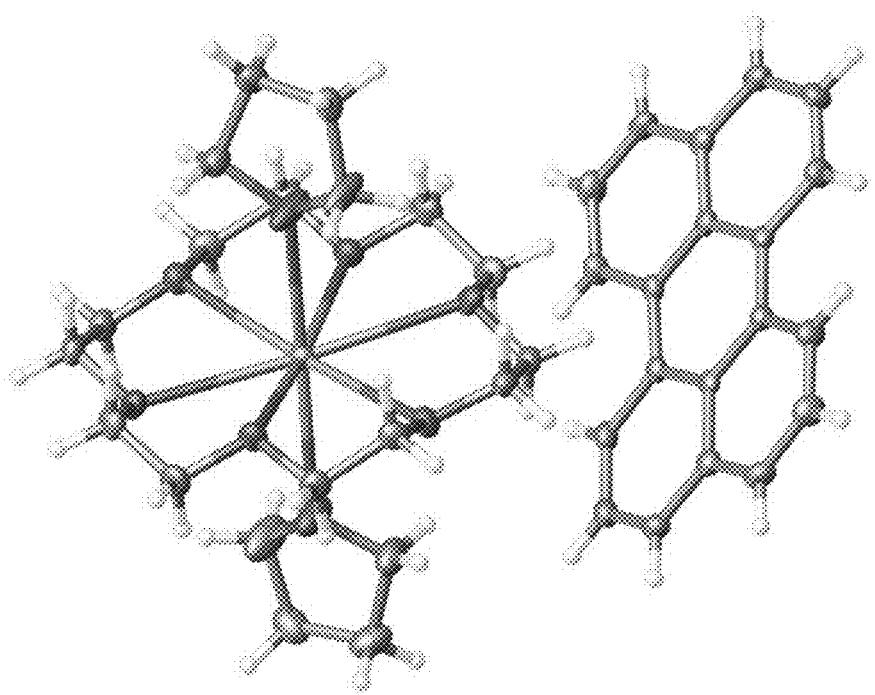

Aromatic hydrocarbons, by virtue of their relatively low-lying π* LUMO, can be readily reduced by alkali metals to give intensely colored, open-shell monoanions. The first well-defined arene radical, viz sodium anthracenide, was reported in 1914 by Wilhelm Schlenk during the formative years of organometallic chemistry.[1] Over a century later, the chemistry of arene radicals continues to command attention. From an electronic perspective, these species display unique aromatic character and have been shown to exhibit long-range magnetic ordering in the solid-state.[2] Chemically, arene radicals find utility in a wide range of applications including use as initiators in anionic polymerization,[3] as potent organic reducing agents and bases,[4] models for graphitic battery materials,[5] and are key intermediates in Birch reductions.[6]

Given the radical nature of arene monoanions, it is well-known that these compounds are highly sensitive and prone to adventitious oxidation, thus requiring preparation and handling under rigorously anaerobic and anhydrous conditions. These reagents are kinetically unstable, having short storage times,[4b] and are often freshly prepared in-situ (necessitating multi-step titration to accurately determine concentration) with product equilibriums that are highly solvent dependent.[1c,7] Moreover, attempts to isolate them from solution often results in disproportionation.[7b] It is not then surprising that only a handful of radical arene mono-anions, utilizing a variety of metals and arenes, have been isolated and characterized in the solid-state.[2b-f,6,8]

These complicating factors negatively affect the utility of these reagents. In order to circumvent many of the aforementioned issues, a general procedure was developed for the solid-state isolation of arene radicals. Described herein is a synthetic method for solid-state structures using twelve arene radical monoanions as examples, as well the characterization of the same.

Initially, the storage of concentrated THF solutions of M[arene$^-$] (M=Li, Na, K; arene=biphenyl, naphthalene, anthracene) at −25° C. produced large, crystalline blocks of the respective anion within hours. However, all attempts to isolate these crystals failed as the solids were observed to rapidly desolvate within seconds upon removal from solution, producing intractable gummy, oils.

The inventors contemplated that desolvation effects could be mitigated by addition of a chelating base to sequester the alkali metal cations and protect their coordination sphere from solvent loss. Accordingly, treatment of M[arene$^-$] in THF with 1 equiv of 18-crown-6 and subsequent storage at −25° C. affords crystalline solids of [M(18-c-6)(THF)$_n$][arene$^-$] (eq 1) in all cases. Gratifyingly, upon removal from solution and drying under vacuum, the products retain their shape and form. While 18-crown-6 has been previously employed for the successful solid-state isolation of the potassium complexes [K(18-c-6)(THF)$_2$][C$_{10}$H$_8$] and [K(18-c-6)(THF)$_2$][C$_{14}$H$_{10}$],[2b] the inventors have found this common and relatively inexpensive reagent suitable for use with both lithium and sodium metals, thus avoiding the need for specialized and size-specific crown ethers in these reactions.

(1)

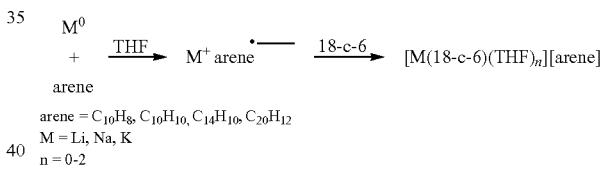

arene = C$_{10}$H$_8$, C$_{10}$H$_{10}$, C$_{14}$H$_{10}$, C$_{20}$H$_{12}$
M = Li, Na, K
n = 0-2

The number of ancillary solvent molecules in [M(18-c-6)(THF)$_n$][arene$^-$] cannot be readily quantified by NMR spectroscopy due to significant signal broadening, a consequence of the compounds' inherent paramagnetism. On the other hand, the high crystallinity of these compounds makes them very amenable to X-ray diffractometry, thus allowing for unambiguous composition determination (Table 1).

TABLE 1

Isolated Arene Radical Monoanions and Electronic Properties.

| Compound | % Yield | $E_{1/2}$ (V)$^a$ | λ (nm) | $\mu_{eff}$ ($\mu_B$)$^b$ |
|---|---|---|---|---|
| [Li(18-c-6)][C$_{10}$H$_8$] (1) | 37 | −3.09 | 294, 318, 327, 376, 435, 468, 799 | 1.53 |
| [Na(18-c-6)(DME)][C$_{10}$H$_8$] (2) | 79 | −3.09 | 294, 327, 373, 442, 469, 798, 875 | 1.67 |
| {[K(18-c-6)][μ:η$^2$-C$_{10}$H$_8$]}$_\infty$ (3) | 80 | −3.13 | 294, 326, 374, 445, 469, 771, 856 | 2.11 |
| [Li(κ$^3$-18-c-6)(THF)$_2$][C$_{12}$H$_{10}$] (4) | 42 | −3.18 | 411, 643, 829 | 2.08 |
| [Na(18-c-6)(THF)$_2$][C$_{12}$H$_{10}$] (5) | 53 | −3.15 | 410, 451, 653, 837 | 2.24 |
| [K(18-c-6)(THF)$_2$][C$_{12}$H$_{10}$] (6) | 37 | −3.17 | 403, 649, 831 | 2.20 |
| [Li(18-c-6)][C$_{14}$H$_{10}$] (7) | 30 | −2.53 | 328, 348, 358, 369, 407, 550, 598, 641, 659, 696, 735, 759, 813, 921 | 1.67 |
| [Na(18-c-6)(DME)][C$_{14}$H$_{10}$] (8) | 87 | −2.48 | 329, 342, 353, 359, 368, 379, 407, 546, 595, 638, 659, 698, 728, 752, 813, 922 | 1.90 |
| [K(18-c-6)(THF)$_2$][C$_{14}$H$_{10}$] (9)$^c$ | 31 | −2.49 | 328, 348, 358, 367, 407, 550, 598, 640, 661, 698, 733, 759, 813, 925 | 1.97 |
| [Li(κ$^3$-18-c-6)(DME)][C$_{20}$H$_{12}$]•0.5C$_{20}$H$_{12}$ (10) | 55 | −2.20, −2.87 | 322, 388, 411, 437, 579, 688, 740, | 2.20 |

TABLE 1-continued

Isolated Arene Radical Monoanions and Electronic Properties.

| Compound | % Yield | $E_{1/2}$ (V)[a] | λ (nm) | $\mu_{eff}(\mu_B)$[b] |
|---|---|---|---|---|
| [Na(18-c-6)(DME)][$C_{20}H_{12}$] (11) | 84 | −2.19, −2.77 | 761, 782, 813, 847, 903, 1007 323, 393, 414, 438, 465, 580, 692, 737, 782, 813, 849, 906, 1010 | 2.29 |
| [K(18-c-6)(THF)$_2$][$C_{20}H_{12}$] (12) | 38 | −2.28, −2.80 | 323, 393, 413, 438, 580, 689, 741, 757, 778, 812, 847, 903, 1008 | 2.10 |

[a]Referenced vs Fc[0/+].
[b]Guoy balance measurement.
[c]Known structure, see reference 2b.

Crystals of [M(18-c-6)(THF)$_n$][arene$^{-•}$] harvested from THF solutions are typically of satisfactory size and shape for X-ray crystallographic analyses. In a few instances, most often with the lithium and sodium salts of naphthalene and perylene, fine needles too small for crystallographic characterization are produced. However, recrystallization of these compounds from DME solutions does yield X-ray quality crystals.[9]

Examination of the solid-state structures of 1-12 (see FIG. 1) reveals that nearly all crystallize as non-interacting ion pairs with one notable exception. In 3, the [K(18-c-6)]$^+$ moiety is axially flanked by two bridging [$C_{10}H_8$]$^{-•}$ anions forming a close contact network that gives rise to a 1D coordination polymer. Interestingly, each of the two bridging naphthalenes exhibits a distinct coordination mode. The first naphthalene ligates the potassium cations through η$^2$-binding where the two K—C$_{arene}$ bond distances (avg. 3.13 Å) and K—C$_{arene}$ dihedral angle (120.30) are indicative of a typical π-cation interaction. The second naphthalene engages each potassium through two longer K—C$_{arene}$ bonds (avg. 3.45 Å) with a notably more obtuse K—C$_{arene}$ dihedral angle (150.3°), parameters that are consistent with agostic interactions between potassium and the C—H bonds of the naphthalene.[10] It should be noted that the ion-separated analog [K(18-c-6)(THF)$_2$][$C_{10}H_8$] has been reported.[2b] While the exact cause of this structural variation is not known, the difference is attributed to differing crystallization methods and conditions.[2b,9]

Yields of 1-12 fall within a wide range, from moderate to excellent (Table 1), with diminished yields most often a result of solution equilibrium effects or high solubility in THF.[1c,7b] In contrast to standing solutions, 1-12 can be stored as solids under nitrogen for extended periods of time. When kept under strictly anhydrous and anaerobic conditions, it was have found that solid samples of 1-12 were unchanged after almost a year.

The solution redox properties of each complex were examined by cyclic voltammetry (CV). In all cases, the compounds exhibit chemically reversible ($i_{pc}/i_{pa}$≈1) redox waves with $E_{1/2}$ values in full agreement with known reduction potentials.[1c,4b,9] While it has been suggested that the identity of the alkali cation should have a detectable effect on the potential values,[4b] the inventors observe no systematic effects under their experimental conditions.[9] As anticipated, the reducing power of the arene radical monoanions follows the trend $C_{20}H_{12}^{-•}<C_{14}H_{10}^{-•}<C_{10}H_8^{-•}<C_{12}H_{10}^{-•}$ (Table 1). It should be noted that while complexes 1-12 each have chemically accessible dianionic forms, we find only the perylene derivatives 10-12 display a second redox wave in their CV in THF at room temperature.

The signature electronic absorption features of each arene$^{-•}$ type are seen in the UV-vis/NIR solution spectra of 1-12 (Table 1).[1c,11] Between the complexes within a given arene$^{-•}$ class (e.g. 1 vs 2 and 3) the spectra are qualitatively similar; notably, though, the peak definitions and absorbance parameters are found to be cation dependent (without systematic trend). While these observations stand in contrast to the results found in the respective CV data, the electrochemical experiments are conducted in the presence of a vast excess of supporting electrolyte which may impede close M-arene$^{-•}$ pairing.

The solid-state, room temperature magnetic susceptibilities of the open-shell compounds were measured (Gouy balance). The effective magnetic moments of 1-12 are unexceptional and found to range from 1.53 to 2.28$\mu_B$. These values are comparable to that found for [K$_2$(THF)][$C_{10}H_8$] (1.69$\mu_B$ per anion) and fall in line with the 1.7$\mu_B$ calculated for an isolated S=½ system.[2c]

Following the protocol recently developed by Buchwald and co-workers for the sealing of air-sensitive palladium catalysts in paraffin as an oxygen and water exclusion barrier,[12] it was found that the described arene radical monoanions can be sealed in paraffins, e.g. eicosane, and stored in air for at least several days without detectable degradation. By this method of encasing these arenides in paraffins, storage under aerobic and hydrous atmospheric conditions without specialized equipment becomes possible. Moreover, these paraffin mixtures can be used as easily handled delivery agents for chemical reactions and processes.

The inventors have described a general and straightforward procedure for the solid-state isolation of arene radical monoanions using 18-crown-6 as a co-reagent. As proof of principle, the inventors have demonstrated through twelve examples that the methodology can be applied to a wide range of aromatic systems with varying counter cations to give highly crystalline, well-defined materials. These solids, as compared to their parent solutions, are remarkably stable, easily stored, and readily handled—further enhancing the utility of these novel and important radical species.

REFERENCES 1. (a) Schlenk, W.; Appenrodt, J.; Michael, A.; Thal, A. *Ber. Dtsch. Chem. Ges.* 1914, 47, 473; (b) Scott, N. D.; Walker, J. F.; Hansley, V. L. *J. Am. Chem. Soc.* 1936, 58, 2442; (c) Holy, N. L. *Chem. Rev.* 1974, 74, 243.
2. (a) Soncini, A.; Fowler, P. W. *Chem. Phys. Lett.* 2008, 450, 431; (b) Rosokha, S. V.; Kochi, J. K. *J. Org. Chem.* 2006, 71, 9357; (c) Scott, T. A.; Ooro, B. A.; Collins, D. J.; Shatruk, M.; Yakovenko, A.; Dunbar, K. R.; Zhou, H. C. *Chem. Commun.* 2009, 65; (d) Bock, H.; Gharagozloo-Hubmann, K.; Sievert, M.; Prisner, T.; Havlas, Z. *Nature* 2000, 404, 267; (e) Melero, C.; Guijarro, A.; Yus, M.

*Dalton Trans.* 2009, 1286; (f) de Boer, E.; Klaassen, A. A. K.; Mooij, J. J.; Noordik, J. H. In *Pure Appl. Chem.* 1979; Vol. 51, p 73.
3. Baskaran, D.; Mtiller, A. H. E. Anionic Vinyl Polymerization In *Controlled and Living Polymerizations*; Wiley-VCH Verlag GmbH & Co. KGaA: 2010, p 1.
4. (a) Kowalczuk, M.; Kurcok, P.; Glowkowski, W.; Jedlinski, Z. *J. Org. Chem.* 1992, 57, 389; (b) Connelly, N. G.; Geiger, W. E. *Chem. Rev.* 1996, 96, 877.
5. Zabula, A. V.; Filatov, A. S.; Spisak, S. N.; Rogachev, A. Y.; Petrukhina, M. A. *Science* 2011, 333, 1008.
6. Krieck, S.; Kretschmer, R.; Gorls, H.; Westerhausen, M. *J. Am. Chem. Soc.* 2011, 133, 6960.
7. (a) Rainis, A.; Szwarc, M. *J. Am. Chem. Soc.* 1974, 96, 3008; (b) Grovenstein, E. With Adducts of Conjugated Hydrocarbons in Donor Solvents In *Inorganic Reactions and Methods*; John Wiley & Sons, Inc.: 2007, p 160.
8. Hitchcock, P. B.; Lappert, M. F.; Protchenko, A. V. *J. Am. Chem. Soc.* 2001, 123, 189.
9. See supporting information for details.
10. Loh, C.; Seupel, S.; Görls, H.; Krieck, S.; Westerhausen, M. *Organometallics* 2014, 33, 1480.
11. Balk, P.; Hoijtink, G. J.; Schreurs, J. W. H. *Rcl. Trav. Chim.* 1957, 76, 813.
12. Sather, A. C.; Lee, H. G.; Colombe, J. R.; Zhang, A.; Buchwald, S. L. *Nature* 2015, 524, 208.

The invention claimed is:
1. A composition comprising a crystalline solid having a formula:

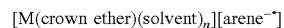

[M(crown ether)(solvent)$_n$][arene$^{-\cdot}$]

wherein M is an alkali metal selected from lithium, sodium, or potassium;
crown ether is selected from 18-crown-6 polyether, 15-crown-5 polyether, or 12-crown-4 polyether;
the solvent is a polar, coordinating organic solvent;
n is 1, 2, 3, 4, 5, or 6; and
the arene radical is a biphenyl, naphthalene, anthracene, or perylene radical.
2. The composition of claim 1, wherein the crown ether is 18-crown-6 polyether.
3. The composition of claim 1, wherein the alkali metal is lithium.
4. The composition of claim 1, wherein the arene is naphthalene.

\* \* \* \* \*